US006770606B2

(12) United States Patent
Koduvely et al.

(10) Patent No.: US 6,770,606 B2
(45) Date of Patent: Aug. 3, 2004

(54) LOW DENSITY DETERGENT COMPOSITION

(75) Inventors: Hari Koduvely, Bangalore (IN); Suresh Murigeppa Nadakatti, Bangalore (IN); Vijay Mukund Naik, Bangalore (IN); Prassana Pathak, Bangalore (IN); Shiju Thomas, Bangalore (IN)

(73) Assignee: Unilever Home & Personal Care USA, a division of Conopco, Inc., Greenwich, CT (US)

( * ) Notice: Subject to any disclaimer, the term of this patent is extended or adjusted under 35 U.S.C. 154(b) by 23 days.

(21) Appl. No.: 10/118,322

(22) Filed: Apr. 9, 2002

(65) Prior Publication Data

US 2002/0198120 A1 Dec. 26, 2002

(30) Foreign Application Priority Data

Apr. 10, 2001 (IN) .................................. 322/MUM/2001

(51) Int. Cl.[7] .................................................. A61K 7/50

(52) U.S. Cl. ....................... 510/141; 510/145; 510/152; 510/155

(58) Field of Search ................................ 510/130, 141, 510/152, 155, 153, 156, 147

(56) References Cited

U.S. PATENT DOCUMENTS

| | | | | |
|---|---|---|---|---|
| 2,295,594 A | | 9/1942 | Mills | 252/368 |
| 2,525,081 A | | 10/1950 | Schulerud | 252/370 |
| 3,066,354 A | * | 12/1962 | Chaffee | 18/47.5 |
| 5,972,860 A | | 10/1999 | Eshita et al. | 510/145 |

FOREIGN PATENT DOCUMENTS

| | | | |
|---|---|---|---|
| EP | 0 848 056 A2 | | 6/1998 |
| FR | 2780411 | | 12/1999 |
| WO | WO 01/11001 | * | 2/2001 |

OTHER PUBLICATIONS

Abstracts of Japan, Publication No. 2002–012889, Publication Date Jan. 15, 2002.

* cited by examiner

*Primary Examiner*—Necholus Ogden
(74) *Attorney, Agent, or Firm*—Alan Bornstein

(57) ABSTRACT

Aerated, ultra low-density cast-dehydrated syndet detergent bars for use in personal wash, fabric wash and hard surface cleaning. A process for preparing aerated, ultra low-density cast-dehydrated detergent bars wherein the air is entrained in the bars after rigidification and shaping the product is also provided.

10 Claims, No Drawings

LOW DENSITY DETERGENT COMPOSITION

TECHNICAL FIELD

The present invention relates to aerated ultra low density cast-dehydrated detergent bars. The invention particularly relates to a process for preparing aerated ultra low density cast-dehydrated detergent bars wherein the air is entrained in the bars after rigidification and shaping the product.

BACKGROUND AND PRIOR ART

Soap or non-soap detergent articles are traditionally produced by shear working/homogenisation of the formulation followed by extrusion and stamping. This procedure is only suitable for detergent bar formulations which are thermoplastic or which are not shear sensitive. The formulations that are shear sensitive are generally produced by the process of casting. In the manufacture of detergent compositions by casting the formulated system is taken to a fluid state by raising the temperature, filled into moulds, and cooled.

The water content in the detergent bars is generally maintained around 5–40%. If gases such as air can be entrapped in the detergent bar the bulk density of the bar can be reduced and it enables the manufacture of larger size bars for a given weight. It is also possible to entrap sufficient air in order to make the bars float in the washing solution. The concept of entrapment of air or gas has been achieved more particularly for soap bars as it is an advantage to have the bars float in the bath tub.

U.S. Pat. No. 2,295,594 (P&G, 1942) discloses a process for obtaining floating soap comprising mechanical air entrapment through whipping and extrusion of soap in a condition of pasty cohesiveness such that air in finely divided bubble form can be incorporated. The bars are allowed to cool and harden after extrusion. The soap bar compositions do not contain any non-soap detergent active.

U.S. Pat. No. 5,972,860 (Kao Corporation, 1999), discloses aerated detergent bar essentially incorporating inorganic salts and/or polyols and non-ionic surfactants wherein the air is in the fine bubble form and is entrapped in the formulation before casting.

U.S. Pat. No. 5,194,172 (P&G, 1990) discloses an aerated freezer bar comprising fatty acid soap, sucrose, hydrophobic material selected from waxes, and water.

U.S. Pat. No. 5,219,487 (P&G, 1992) discloses an aerated freezer soap bar comprising fatty acid soap, free fatty acid, salt, and water.

The prior art generally teaches compositions and manufacture of aerated soap bars wherein air entrapment in fine bubble form prior to rigidification and shaping of the product is essential. Air entrapment prior to shaping limits the formulation flexibility and requires special purpose equipment to provide mechanical agitation for whipping in air that makes the process capital intensive. The amount of air entrapped is also low and thus detergent bars with ultra low density can not be obtained. It has now been possible to obtain ultra low density cast-dehydrated bars comprising fatty acid soap, non soap detergent active, and very high amount of air, wherein the air is entrained in to the bars after rigidification and shaping of the product. This technology provides formulation flexibility and results in ultra low-density bars that can be produced economically.

DESCRIPTION OF THE INVENTION

According to one aspect of the present invention there is provided an ultra low density cast-dehydrated detergent bar composition comprising:

i 10–60% by volume a neutralised carboxylic fatty acid with chain length $C_8$–$C_{24}$, ii 0–40% by volume non-soap surfactant, and iii 1–90% by volume air According to a preferred aspect of the invention the said neutralised carboxylic fatty acid comprises at least 50% saturated fatty acid with $C_{16}$–$C_{24}$ chain length, more preferably 70% is a saturated fatty acid with $C_{16}$–$C_{20}$ chain length and the said non-soap surfactant is at least 1% and up to 40%.

In the formulation it is particularly preferred that the ratio of soap to non-soap detergent active is greater than 0.5.

According to another aspect of the present invention there is provided a process for preparing an ultra low density cast-dehydrated detergent bar comprising the steps of:

i. heating a mixture comprising (a) 10–60% by weight a neutralised carboxylic fatty acid with chain length $C_8$–$C_{24}$, (b) 0–40% by weight non-soap surfactant, and (c) 1–90% by weight water, to a temperature in the range 50–100° C. to obtain a pourable melt, ii. pouring the said melt into a mould, iii. cooling the melt to bring about rigidification, and iv. dehydrating the rigid bar to bring down the moisture level to enable entrainment of air in the range 1–90% by volume of the composition.

Preferably the density of the detergent bars of the invention is less than 0.9 g/cc, more preferred less than 0.8 g/cc, even more preferred from 0.25 to 0.70 g/cc

DETAILED DESCRIPTION OF THE INVENTION

The essential feature of the present invention relates to aerated ultra low density cast-dehydrated syndet detergent bars comprising soap and/or non-soap and air wherein the air is incorporated in the bars after shaping the product. The soap is a neutralised carboxylic fatty acid with chain length $C_8$–$C_{24}$ wherein preferably at least 50% and more preferably 70% is a saturated fatty acid with $C_{16}$–$C_{20}$ chain length. The invention also relates to a process for preparing the said aerated ultra low density cast-dehydrated detergent bar.

The composition according to the invention is suitable for personal wash, fabric wash and hard surface cleaning.

Fatty Acid Soap

The fatty acid soap is preferably selected from one or more salts of saturated $C_8$–$C_{24}$ fatty acids. The soap employed may be a sodium, potassium, magnesium, aluminium, calcium or lithium salt of saturated fatty acids. It is especially preferred to have soap obtained as sodium or potassium salt of saturated fatty acid. The soap is present at 10–60% by volume of the composition and is preferably at 15–40%. It is preferred that at least 50% and more preferably 70% of the soap is obtained from neutralised saturated fatty acid with $C_{16}$–$C_{20}$ chain length.

In the formulation it is particularly preferred that the ratio of soap to non-soap detergent active is greater than 0.5.

Non Soap Detergent Active

It is preferable to employ non-soap detergent actives that are selected from anionic, non-ionic, cationic, amphoteric or zwitterionic surfactants or their mixtures in the range 1–40% by volume.

Suitable anionic detergent active compounds are water soluble salts of organic sulphuric reaction products having in the molecular structure an alkyl radical containing from 8 to 22 carbon atoms, and a radical chosen from sulphonic acid or sulphuric acid ester radicals and mixtures thereof. Some examples of synthetic anionic detergent active compounds are linear alkyl benzene sulphonate, Sodium lauryl sulphate, Sodium lauryl ether sulphate, Alpha olefin sulphonate, alkyl ether sulphate, Fatty methyl ester sulphonate, Alkyl isothionate, Sulphosuccinates, etc.

The cations most suitable in above detergent active species are sodium, potassium, ammonium, and various amines e.g. monoethanol amine, diethanolamine and triethanolamine.

Suitable non-ionic detergent active compounds can be broadly described as compounds produced by the condensation of alkylene oxide groups, which are hydrophilic in nature, with an organic hydrophobic compound which may be aliphatic or alkyl aromatic in nature. The common non-ionic surfactants are the condensation products of aliphatic alcohols having from 8 to 22 carbon atoms in either straight or branched chain configuration with ethylene oxide, such as a coconut oil ethylene oxide condensate having from 2 to 15 moles of ethylene oxide per mole of coconut alcohol. Some examples of non-ionic surfactants are Alkyl phenol ethylene oxide (EO) condensate, Tallow alcohol 10 EO condensate, Alkyl de-methyl amine oxides, Lauryl mono-ethanolamide, Sugar esters, etc.

Some examples of amphoteric detergent active are Coco amidopropyl betaine, Cocobetaine, etc.

It is also possible optionally to include cationic or zwitterionic detergent actives in the compositions according to the invention.

Further examples of suitable non-soap detergent active species are given in the following reference: "Handbook of Surfactants", M. R. Porter, Chapman and Hall, New York, 1991.

The non-soap detergent active to be employed in the detergent composition of this invention is preferably anionic and will generally be up to 40% (v/v) and more preferably from 2 to 30%.

Optional Ingredients

Other optional ingredients such as salting-in-electrolytes, polyols, fillers, colour, perfume, opacifier, preservatives, one or more water insoluble particulate materials such as talc, kaolin, polysaccharides, liquid benefit agents such as sunscreen agents, moisturisers, emollients, anti-ageing compounds, hair conditioning agents, and other conventional ingredients may be incorporated in the composition.

Detergent bars of the invention can be made without the need of high levels of polyol solvents, such as glycerol or sorbitol. Preferably the compositions are substantially free from polyol solvents i.e. level of polyols is less than 10% volume of the composition especially preferred less than 5 vol % or even less than 1 vol %, most preferred substantially 0 vol %.

Also detergent bars of the invention can be made without the need of high levels of salts, preferably the compositions are substantially free from salts i.e. the level of salts is less than 10% volume of the composition especially preferred less than 5 vol % or even less than 1 vol %, most preferred substantially 0 vol %.

Process

The mixture comprising soap, non-soap surfactant and water is heated to obtain a pourable melt and is cast into a rigid bar/block by using a suitable rigid or flexible mould. The mould may be suitably selected to produce near net shape tablet or to produce bars/blocks. The bars/blocks may be further shaped in to detergent article.

It is possible to start with soap and non-soap surfactants or the acid precursors of the same. If acid precursors of soap and non soap surfactant were used, then neutralisation of fatty acids was carried out at elevated temperatures of ~80° C. and pH of the melt was adjusted in the range 9.5 to 10.5.

The rigid detergent article is dehydrated either at room temperature or at elevated temperatures without affecting the shape of the product to enable entrainment of air. The dehydration process can be expedited by using convective air flow.

The invention will now be illustrated with respect to the following non-limiting examples.

EXAMPLES i. Process of Preparing Aerated Bar

The process consists of preparing a pourable melt of the composition which is cast into desired shape followed by dehydration to achieve entrainment of air.

Table 1a shows compositions at the time of casting, before dehydration (in wt. %) whereas Table 1b shows compositions of the corresponding cast-dehydrated bar (in vol %). The composition of the cast dehydrated bar is given in terms of % volume because a major component of the bar is air. The compositions shown in Table 1b were prepared by the following process.

A mixture of soap, non soap surfactant and water (for all examples except example no. 5a, where only a soap-water mixture was taken) with compositions as shown in Table 1a (compositions in wt. %) was taken in a two liter capacity round bottom flask. The mixture was agitated and heated using a hot water bath to about 80° C. to obtain a pourable melt. This melt was poured into a rectangular mould of following dimensions: length 8 cm, breadth 5 cm and height 4 cm. The melt was allowed to cool to bring about rigidification and the rigidity of all these bars was >75 k Pa.

The rigid bar was then kept in a hot air oven at 45° C. and dehydrated to enable entrainment of air. The process of dehydration was continued until desired level of aeration was achieved. The volume percent composition of the final bar depends upon size reduction during dehydration. The compositions (vol. %) of the resulting ultra low density cast dehydrated bars are shown in Table 1b. The compositions (in vol %) shown in Table 1b were arrived at based on the starting compositions (in wt. % as shown in Table 1a), density of ingredients, and shrinkage during dehydration. The procedures for measurement of yield stress and estimation of density of cast dehydrated bars are described below.

ii. Measurement of Yield Stress

The automatic penetrometer used for yield stress measurements was model PNR 10 from M/s Petrotest Instruments GmbH. Standard Hollow Cone (part # 18-0101, as per ASTM D 217-IP 50) along with Plunger (part # 18-0042) was used for the measurements. The cone consisted of a conical body of brass with detachable, hardened steel tip. The total mass of the cone was 102.5 g. The total mass of the movable plunger was 47.5 g. Total mass of cone and plunger that fall on the detergent tablet was therefore 150 g. Additional weights of 50 g and 100 g (making the total weight falling on the sample 200 g and 250 g, respectively) were also used. The yield stress value of the sample at 25° C. was measured using the standard procedure comprising following steps:

1. The detergent tablet was placed on the table of the penetrometer.
2. The measuring device of the penetrometer was lowered so that the tip of the penetrometer touched the tablet but did not penetrate it.
3. The measurement operation was started by pressing “start” key.
4. The penetration depth was read in mm as indicated on the display.

iii. Estimation of Density of the Bar

The weight of the ultra low density cast dehydrated detergent bar was measured using a balance. The volume of the bar was calculated from the dimensions of the parallelepiped bar. The density was calculated using mass and volume.

TABLE 1a

| Components by Wt. % | Ex 1a | Ex 2a | Ex 3a | Ex 4a | Ex 5a | Ex 6a | Ex 7a | Ex 8a | Ex 9a |
|---|---|---|---|---|---|---|---|---|---|
| Sodium palmitate | 12 | 18 | 28.0 | 27.7 | 25.0 | — | 13.5 | — | 13.0 |
| Sodium hydroxy stearate | — | — | — | | — | 28.0 | — | — | — |
| Sodium stearate | — | — | — | 5.8 | — | — | 16.5 | — | — |
| Sodium laurate | — | — | 6.0 | — | 3.0 | — | | 25 | 15.0 |
| Alpha olefin sulphonate | 2 | 13 | 3.0 | 2.5 | — | 3.0 | 2.0 | 3 | 10.0 |
| Water | 86 | 69 | 62.0 | 63 | 72 | 69 | 67 | 72 | 62.0 |
| NaCl | — | — | 1 | 1 | — | — | 1 | — | — |

TABLE 1b

| Components by Vol. % | Ex 1b | Ex 2b | Ex 3b | Ex 4b | Ex 5b | Ex 6b | Ex 7b | Ex 8b | Ex 9b |
|---|---|---|---|---|---|---|---|---|---|
| Sodium palmitate | 13.3 | 19.4 | 28.0 | 30.4 | 26.3 | — | 18.8 | — | 18.7 |
| Sodium hydroxy staerate | — | — | — | | — | 28.0 | — | — | — |
| Sodium stearate | — | — | — | 6.6 | — | — | 22.9 | — | — |
| Sodium laurate | — | — | 6.0 | — | 3.2 | — | — | 35.7 | 21.4 |
| Alpha olefin sulphonate | 2.9 | 13.9 | 3.0 | 3.0 | — | 3.0 | 2.8 | 4.3 | 14.3 |
| Water | 27.0 | 3.3 | 22.0 | 12.0 | 19 | 10.0 | 17.6 | 60 | 45.7 |
| Air | 56.8 | 63.4 | 40.0 | 47.0 | 51.5 | 59.0 | 36.9 | — | — |
| NaCl | — | — | 1 | 1 | — | — | 1 | — | — |
| Comments | | | | | | | | No air entrainment | No air entrainment |
| Yield Stress @ 25° C. (k Pa) | 342 | 996 | 740 | 680 | 293 | 164 | 986 | 1190 | 698 |
| Density g/cc | 0.43 | 0.4 | 0.61 | 0.5 | 0.51 | 0.4 | 0.6 | 1.04 | 1.09 |

5. The measured penetration depth value was used to calculate the yield stress of the detergent tablet using the following equation:

$$\text{Yield stress}=\text{Applied force}/(\text{Projected area of the cone})=(m\times g)\times 10^3/[\pi(p\tan\tfrac{1}{2}\theta+\tfrac{1}{2}\text{ tip diameter})^2]$$

where

Yield stress is in kPa m: total mass falling on the flat surface of the bar in kg g: acceleration due to gravity in $m/s^2$ p: penetration achieved in mm θ: Cone angle (30°)

tip diameter =0.359 mm

According to the above equation if the measured penetration depth is <10 mm for 200 g total mass falling on the sample then the yield stress of the detergent tablet is >75 kPa. Three yield stress values were calculated for 150 g, 200 g, and 250 g total mass falling on the detergent tablet and the average of the three values was used as the yield stress of the detergent tablet.

Data presented in Tables 1a and 1b show following:

1. Ultra low density cast dehydrated bars with high levels of air according to the invention, can be produced such that the final composition contains neutralised carboxylic fatty acid wherein, preferably at least 50% of the same is a saturated fatty acid with $C_{16}$ (examples 1b to 5b) or $C_{18}$ (examples 6b and 7b) chain length.

2. The water content in the bars at the time of casting is in the range 62–86% (w/w) (examples 1a to 9a).

3. It is preferred that the chain length of the saturated fatty acid is in the range $C_{16}$–$C_{20}$ and if it is below $C_{16}$ as in example 8b it is not always possible to produce ultra low density aerated bars.

4. When the level of neutralised carboxylic acid with chain length $C_{16}$ is less than 50% of the total neutralised carboxylic fatty acid, although other saturated neutralised fatty acid such as $C_{12}$ is present as in example 9b it is not always possible to produce ultra low density aerated bars.

iv. Effect of Various Non-Soap Detergent Actives

Further formulations according to the invention using various non-soap detergent actives are presented in Tables 2a and 2b. Table 2a shows compositions at the time of casting (in wt. %) whereas Table 2b shows compositions of the cast-dehydrated bar (in vol %).

TABLE 2a

| Components by Wt. % | Ex 10a | Ex 11a | Ex 12a | Ex 13a | Ex 14a | Ex 15a | Ex 16a | Ex 17a |
|---|---|---|---|---|---|---|---|---|
| Sodium palmitate | 20 | 40 | 20 | 19 | 20 | 20 | 12 | 20 |
| Sodium laurate | 2 | — | — | — | — | — | — | — |
| Sodium lauryl ether sulphate (SLES) | — | — | 6 | 4.4 | — | — | — | — |
| Cocoamido-propyl betaine (CAPB) | — | — | — | — | 6 | — | — | — |
| Cocomono-ethanol amide (CMEA) | — | — | — | 0.6 | — | — | — | — |
| Cocobetaine | — | — | — | — | — | 6 | — | — |
| Sodium linear alkyl benzene sulphonate (NaLAS) | — | — | — | — | — | — | 3 | 10 |
| Alpha olefin sulphonate | 10 | 3 | — | — | — | — | — | — |
| Water | 68 | 56 | 74 | 76 | 74 | 74 | 85 | 70 |
| NaCl | — | 1 | — | — | — | — | — | — |

TABLE 2b

| Components by Vol % | Ex 10b | Ex 11b | Ex 12b | Ex 13b | Ex 14b | Ex 15b | Ex 16b | Ex 17b |
|---|---|---|---|---|---|---|---|---|
| Sodium palmitate | 25 | 44 | 22 | 21 | 24 | 22 | 12 | 24 |
| Sodium laurate | 2.5 | — | — | — | — | — | — | — |
| Sodium lauryl ether sulphate (SLES) | — | — | 7 | 5.3 | — | — | — | — |
| Cocoamidopropyl betaine (CAPB) | — | — | — | — | 8 | — | — | — |
| Cocomonoethanol amide (CMEA) | — | — | — | 0.7 | — | — | — | — |
| Cocobetaine | — | — | — | — | — | 7 | — | — |
| Sodium linear alkyl benzene sulphonate (NaLAS) | — | — | — | — | — | — | 3 | 12 |
| Alpha olefin sulphonate | 12.5 | 4 | — | — | — | — | — | — |
| Air | 42 | 44 | 66 | 70 | 60 | 66 | 55 | 35 |
| Water | 18 | 7 | 5 | 3 | 8 | 5 | 30 | 29 |
| NaCl | — | 1 | — | — | — | — | — | — |
| Comments | | | | | | | | |
| Yield stress @ 25° C. (kPa) | 686 | 1105 | 848 | 660 | 990 | 948 | 420 | 520 |
| Density (g/cc) | 0.6 | 0.6 | 0.4 | 0.36 | 0.4 | 0.44 | 0.5 | 0.7 |

The data presented in Table 2b show that the ultra-low density cast dehydrated detergent bars with high levels of air can be obtained using different non-soap detergent actives.

What is claimed is:

1. An ultra low density cast-dehydrated detergent bar comprising:

(i) 10–60% by volume of a neutralised $C_8$–$C_{24}$ carboxylic fatty acid;

(ii) 0–40% by volume of a non-soap surfactant; and (iii) 1–90% by volume air wherein at least 50% of the neutralized carboxylic acid is a C16–C20 saturated fatty acid and the air entrained in the bar after rigidification and shaping.

2. A bar according to claim 1 wherein at least 70% of the neutralised carboxylic acid is a $C_{16}$–$C_{20}$ saturated fatty acid.

3. A bar according to claim 1 wherein the non-soap surfactant comprises at least 1%–40% by volume of the composition.

4. A bar according to claim 1 wherein the ratio of soap to non-soap detergent active is greater than 0.5.

5. A bar according to claim 1 wherein the density of the bar is less than 0.9 g/cc.

6. A bar according to claim 1 being substantially free of polyol solvents.

7. A composition according to claim 1, wherein the non-soap surfactant is an anionic surfactant.

8. A composition according to claim 7, wherein the anionic surfactant comprises 2 to 30% by volume of the composition.

9. A process for preparing an ultra low-density cast-dehydrated detergent bar composition according to claim 1 comprising:

(i) heating a mixture of the fatty acid, non-soap surfactant and water to a temperature in the range 50–100° C. to obtain a pourable melt;

(ii) pouring the melt into a mould;

(iii) cooling the melt to bring about rigidification; and (iv) dehydrating the rigid bar to bring down the moisture level to enable entrainment of air in the range 1–90% by volume of the composition.

10. The ultra low density cast-dehydrated detergent bar according to claim 1 wherein said bar has a density of from 0.25–0.70 g/cc and contains less than 1 vol % of polyol solvents.

* * * * *